(12) United States Patent
Ogawa

(10) Patent No.: US 8,465,415 B2
(45) Date of Patent: Jun. 18, 2013

(54) ENDOSCOPE APPARATUS AND MEASUREMENT METHOD

(75) Inventor: Kiyotomi Ogawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 499 days.

(21) Appl. No.: 12/726,774

(22) Filed: Mar. 18, 2010

(65) Prior Publication Data
US 2011/0021873 A1    Jan. 27, 2011

(30) Foreign Application Priority Data
Jul. 23, 2009   (JP) ................ P2009-172174

(51) Int. Cl.
*A61B 1/00* (2006.01)
*A61B 1/04* (2006.01)

(52) U.S. Cl.
USPC ........................... 600/103; 600/109

(58) Field of Classification Search
USPC ............... 600/103, 109, 117; 348/208.99, 348/208.1, 208.6, 305, 320, 322
See application file for complete search history.

(56) References Cited

U.S. PATENT DOCUMENTS

| | | | | |
|---|---|---|---|---|
| 5,034,888 A * | 7/1991 | Uehara et al. | ................. | 600/101 |
| 5,243,666 A * | 9/1993 | Hasegawa et al. | ............ | 382/107 |
| 6,002,425 A * | 12/1999 | Yamanaka et al. | .............. | 348/68 |
| 6,219,091 B1 * | 4/2001 | Yamanaka et al. | .............. | 348/65 |
| 6,234,959 B1 * | 5/2001 | Higuchi et al. | ............... | 600/180 |
| 6,734,894 B1 * | 5/2004 | Higuchi et al. | ................. | 348/69 |
| 7,454,131 B2 * | 11/2008 | Suda | ............... | 396/55 |
| 2005/0231603 A1 * | 10/2005 | Poon | ........................ | 348/208.99 |
| 2007/0195172 A1 * | 8/2007 | Kurata | ..................... | 348/208.99 |
| 2008/0100702 A1 * | 5/2008 | Tannai | ............................ | 348/65 |
| 2008/0151047 A1 | 6/2008 | Bendall | | |
| 2008/0284858 A1 * | 11/2008 | Sasaki et al. | ............... | 348/208.1 |

FOREIGN PATENT DOCUMENTS

| | | |
|---|---|---|
| JP | 08-298616 A | 11/1996 |
| JP | 11-110565 A | 4/1999 |
| JP | 2004-120256 A | 4/2004 |
| JP | 2004-312536 A | 11/2004 |
| JP | 2005-062469 A | 3/2005 |
| JP | 2005-128589 A | 5/2005 |
| JP | 2006-087083 A | 3/2006 |
| JP | 2006-136706 A | 6/2006 |
| JP | 2006-157428 A | 6/2006 |
| JP | 2006-174105 A | 6/2006 |
| JP | 2006-325741 A | 12/2006 |
| JP | 2006-332809 A | 12/2006 |
| JP | 2007-151862 A | 6/2007 |
| JP | 2007-208849 A | 8/2007 |
| JP | 2008-022300 A | 1/2008 |
| JP | 2008-178031 A | 7/2008 |
| JP | 2008-281474 A | 11/2008 |
| JP | 2008-288975 A | 11/2008 |
| WO | 2008/079647 A2 | 7/2008 |

* cited by examiner

*Primary Examiner* — Philip R Smith
(74) *Attorney, Agent, or Firm* — Holtz, Holtz, Goodman & Chick, P.C.

(57) ABSTRACT

An endoscope apparatus according to an aspect of the invention comprises an imaging unit, a detection unit, a process unit, and a measurement unit. The imaging unit comprises an imaging device and generates a first image having two fields by imaging a subject by performing interlaced driving for the imaging device. The detection unit detects the amount of shake of the first image. The process unit generates a second image from the first image based on the amount of shake. The measurement unit measures the subject based on the second image.

7 Claims, 15 Drawing Sheets

US 8,465,415 B2

ENDOSCOPE APPARATUS AND MEASUREMENT METHOD

BACKGROUND OF THE INVENTION

1. Field of the Invention

The present invention relates to an endoscope apparatus and a measurement method that perform a measurement process based on a video signal that is acquired by imaging a subject by using an endoscope.

Priority is claimed on Japanese Patent Application No. 2009-172174, filed Jul. 23, 2009, the content of which is incorporated herein by reference.

2. Description of Related Art

Endoscope apparatuses are used for observing or inspecting an internal damage or corrosion of boilers, turbines, engines, pipes and the like. In addition, there are endoscope apparatuses for measurement that include a function for measuring length, area, or the like by applying the principle of triangulation based on measurement points designated on an image that is imaged by an endoscope. In Japanese Patent Application Laid-Open Publication Nos. 2006-136706 and 2006-325741, an endoscope apparatus for measurement capable of notifying a user whether the distal end of an endoscope approaches an observation target up to a distance appropriate for measurement by displaying a distance (object distance) from the distal end of the endoscope to the subject (observation target) as an observation target in real time has been disclosed.

SUMMARY

In one aspect of the present invention, there is provided an endoscope apparatus that includes at least: an imaging unit which comprises an imaging device and generates a first image having two fields by imaging a subject by performing interlaced driving for the imaging device; a detection unit which detects the amount of shake of the first image; a process unit which generates a second image from the first image based on the amount of shake; and a measurement unit which measures the subject based on the second image.

BRIEF DESCRIPTION OF THE DRAWINGS

The above features and advantages of the present invention will be more apparent from the following detailed description of certain preferred embodiments taken in conjunction with the accompanying drawings, in which.

DETAILED DESCRIPTION OF THE PREFERRED EMBODIMENTS

The invention will be now described herein with reference to illustrative embodiments. Those skilled in the art will recognize that many alternative embodiments can be accomplished using the teachings of the present invention and that the invention is not limited to the embodiments illustrated for explanatory purposes.

Figure 1:
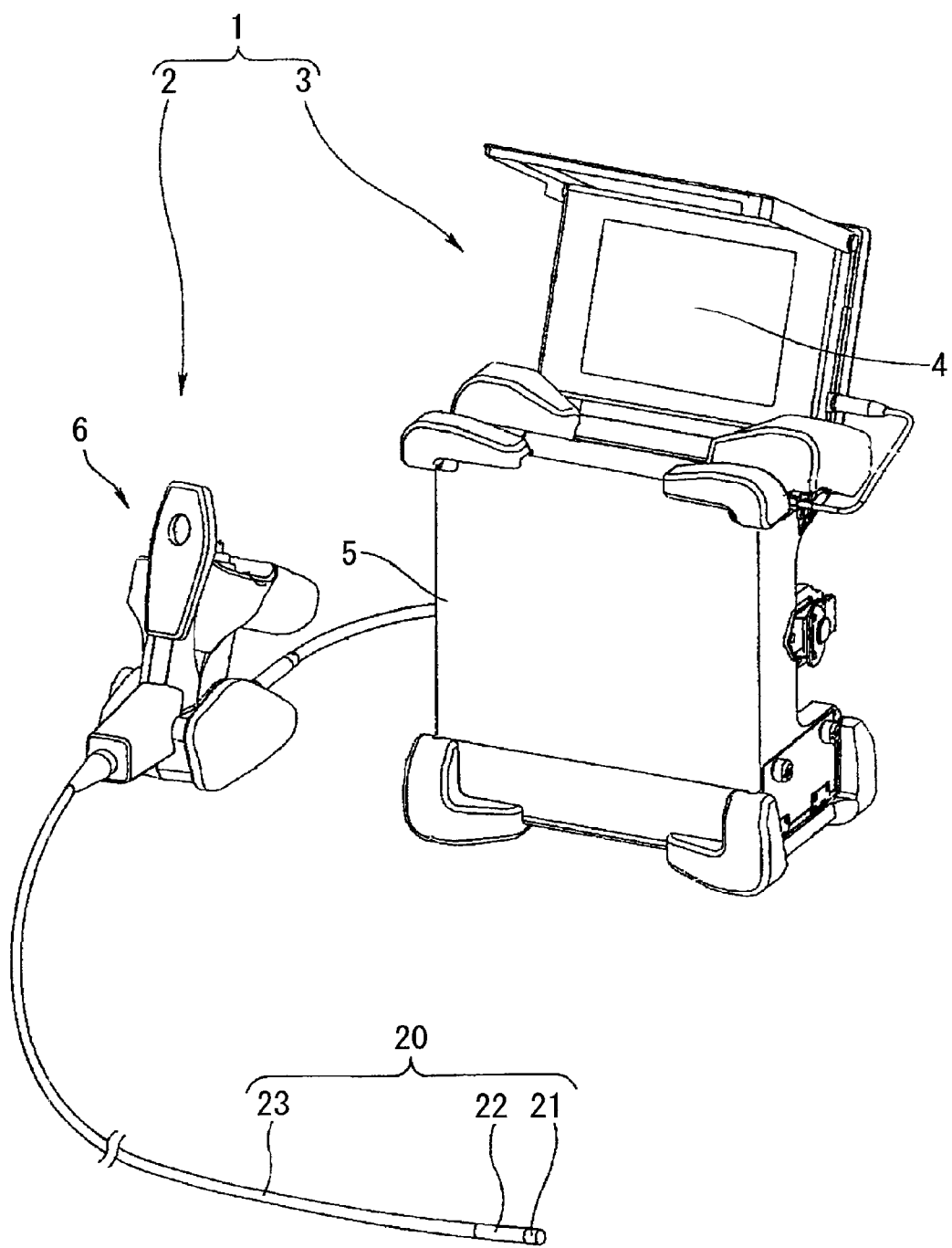
FIG. 1 is a perspective view representing the entire configuration of an endoscope apparatus according to an embodiment of the present invention.

Hereinafter, an embodiment of the present invention will be described with reference to drawings. FIG. 1 represents the entire configuration of an endoscope apparatus according to this embodiment. As shown in FIG. 1, the endoscope apparatus 1 includes an endoscope 2 and a main body 3 that is connected to the endoscope 2. The endoscope 2 includes an insertion portion 20 and an operation portion 6 that is used for performing a control operation for the apparatus. The main body 3 includes a monitor 4 (liquid crystal monitor) that is a display device displaying an image of a subject imaged by the endoscope 2 or information (for example, an operation menu) relating to an operation, and the like and a casing 5 that has a control unit 10 (see FIG. 2) therein.

The insertion portion 20 is configured by sequentially installing a rigid distal end portion 21, a bending portion 22 that can be bent, for example, vertically and horizontally, and a flexible portion 23 that has flexibility from the distal end side so as to be continuous. Various types of optical adapters such as a stereo optical adapter having two observation fields of view and an optical adapter having one observation field of view can be detachably attached to the distal end portion 21.

Figure 2:
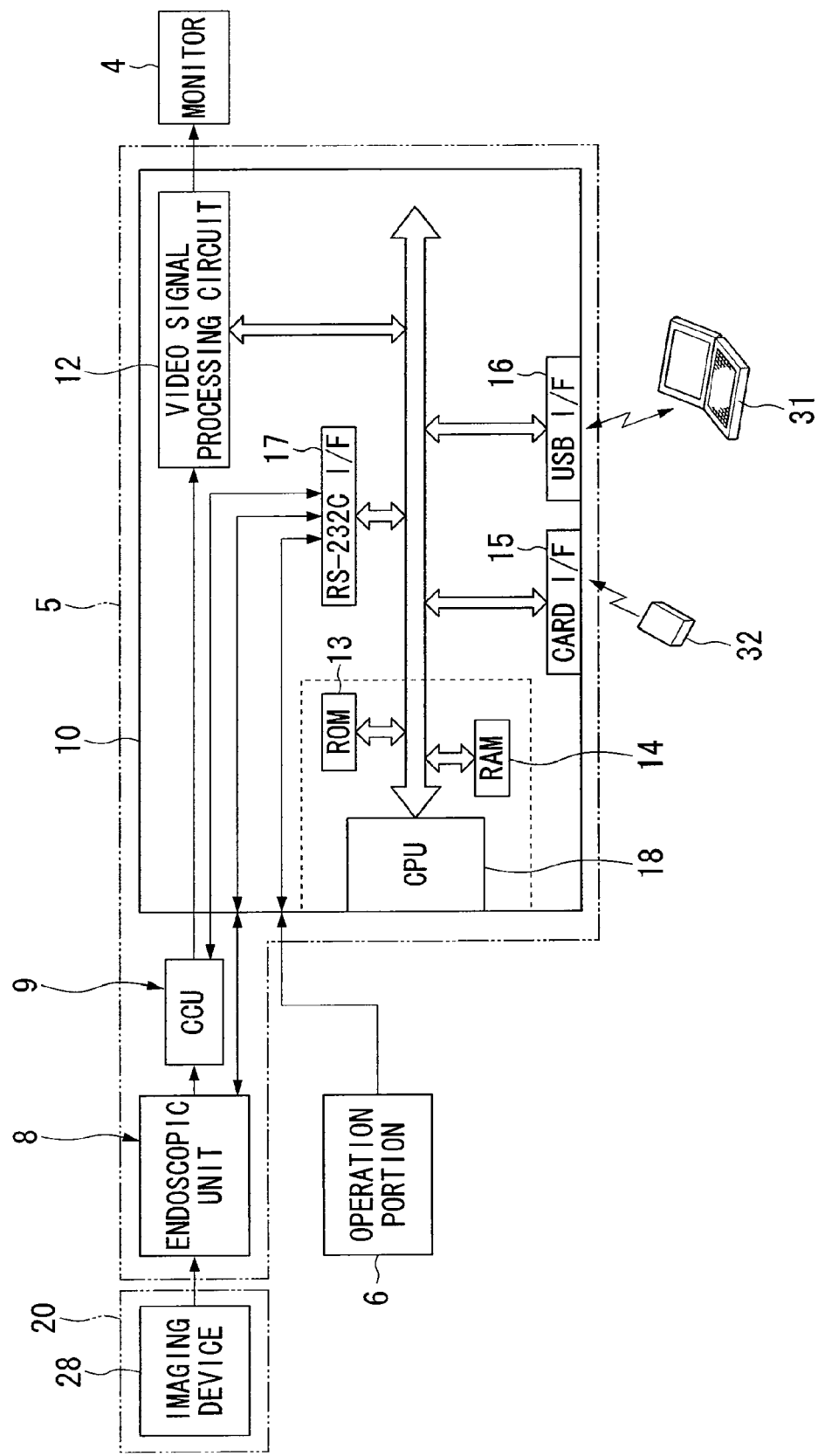
FIG. 2 is a block diagram representing the internal configuration of an endoscope apparatus according to an embodiment of the present invention.

As shown in FIG. 2, an endoscopic unit 8, a CCU 9 (camera control unit), and the control unit 10 are disposed inside the casing 5. A proximal end portion of the insertion portion 20 is connected to the endoscopic unit 8. The endoscopic unit 8 includes a light source driving device that drives a light source built in the distal end portion 21 and a bending device that bends the bending portion 22 included in the insertion portion 20. The CCU 9 includes an imaging-device driving device that performs interlaced driving for an imaging device 28.

The imaging device 28 is built in the distal end portion 21. The imaging device 28 performs photoelectric conversion for a subject image located through the optical adapter so as to generate an image signal. The imaging device 28 outputs an image signal of an odd field and an image signal of an even field in an alternating manner in accordance with the interlaced driving. The image signal that is output from the imaging device 28 is input to the CCU 9. This image signal is converted into a video signal (image data) such as an NTSC signal inside the CCU 9, and the converted image signal is supplied to the control unit 10. In addition, a light source such as an LED that emits luminance light is built in the distal end portion 21.

A video signal processing circuit 12 to which a video signal is input, a ROM 13, a RAM 14, a card I/F 15 (card interface), a USB I/F 16 (USB interface), an RS-232C I/F 17 (RS-232C interface) and a CPU 18 that controls the endoscope apparatus 1 by performing various functions based on programs are disposed inside the control unit 10.

The CCU 9 and the endoscopic unit 8 are connected to the RS-232C I/F 17, and the operation portion 6 that performs control and operation direction for the CCU 9, the endoscopic unit 8, and the like are additionally connected thereto. When a user operates the operation portion 6, the operation portion 6 performs communication needed for controlling the CCU 9 and the endoscopic unit 8 in accordance with the type of the operation.

The USB I/F 16 is an interface that is used for electrically connecting the control unit 10 and a personal computer 31 together. By connecting the control unit 10 and the personal computer 31 through the USB I/F 16, a direction for displaying an endoscopic image on the personal computer 31 or various directions for image processing, for example, at the time of measurement can be made. In addition, input and/or output of control information, data, and the like that are needed for various processes between the control unit 10 and the personal computer 31 can be performed.

In addition, a memory card 32 can be freely attached to or detached from the card I/F 15. By mounting the memory card 32 to the card I/F 15, loading of data such as control information or image data that is stored in the memory card 32 into the control unit 10 or recording of data such as control information or image data into the memory card 32 can be performed under the control of the CPU 18.

The video signal processing circuit 12, in order to display a synthetic image acquired by synthesizing an endoscopic image on the basis of the video signal supplied from the CCU 9 and an operation menu formed by graphics, performs a process for synthesizing a graphic image signal that is generated under the control of the CPU 18 based on the operation menu and a video signal transmitted from the CCU 9, performs a process that is needed for displaying the synthetic image on the screen of the monitor 4, and the like, and supplies a display signal to the monitor 4. In addition, this video signal processing circuit 12 can perform a process for displaying an image alone such as an endoscopic image or an operation menu. As a result, on the screen of the monitor 4, an endoscopic image, an operation menu, a synthetic image acquired by synthesizing an endoscopic image and an operation menu, and the like are displayed. The monitor 4 according to this embodiment can show a video signal that is generated by performing interlaced driving.

The CPU 18 performs control of the endoscope apparatus 1 by controlling various circuit units so as to perform processes for different purposes by executing programs that are stored in the ROM 13. The RAM 14 is used as a work area that is used for temporary data storage by the CPU 18.

Figure 3:
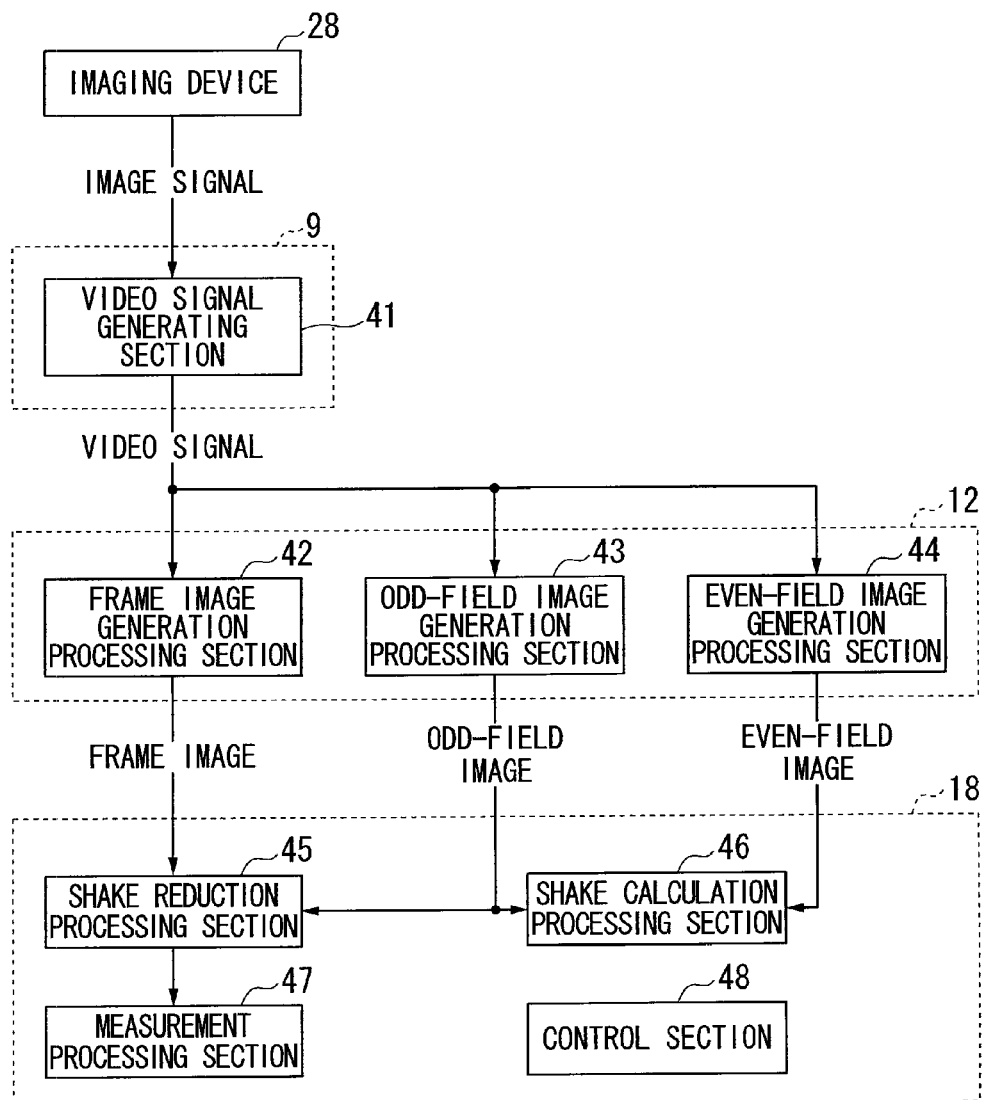
FIG. 3 is a block diagram representing the functional configuration of an endoscope apparatus according to an embodiment of the present invention.
Figure 4:
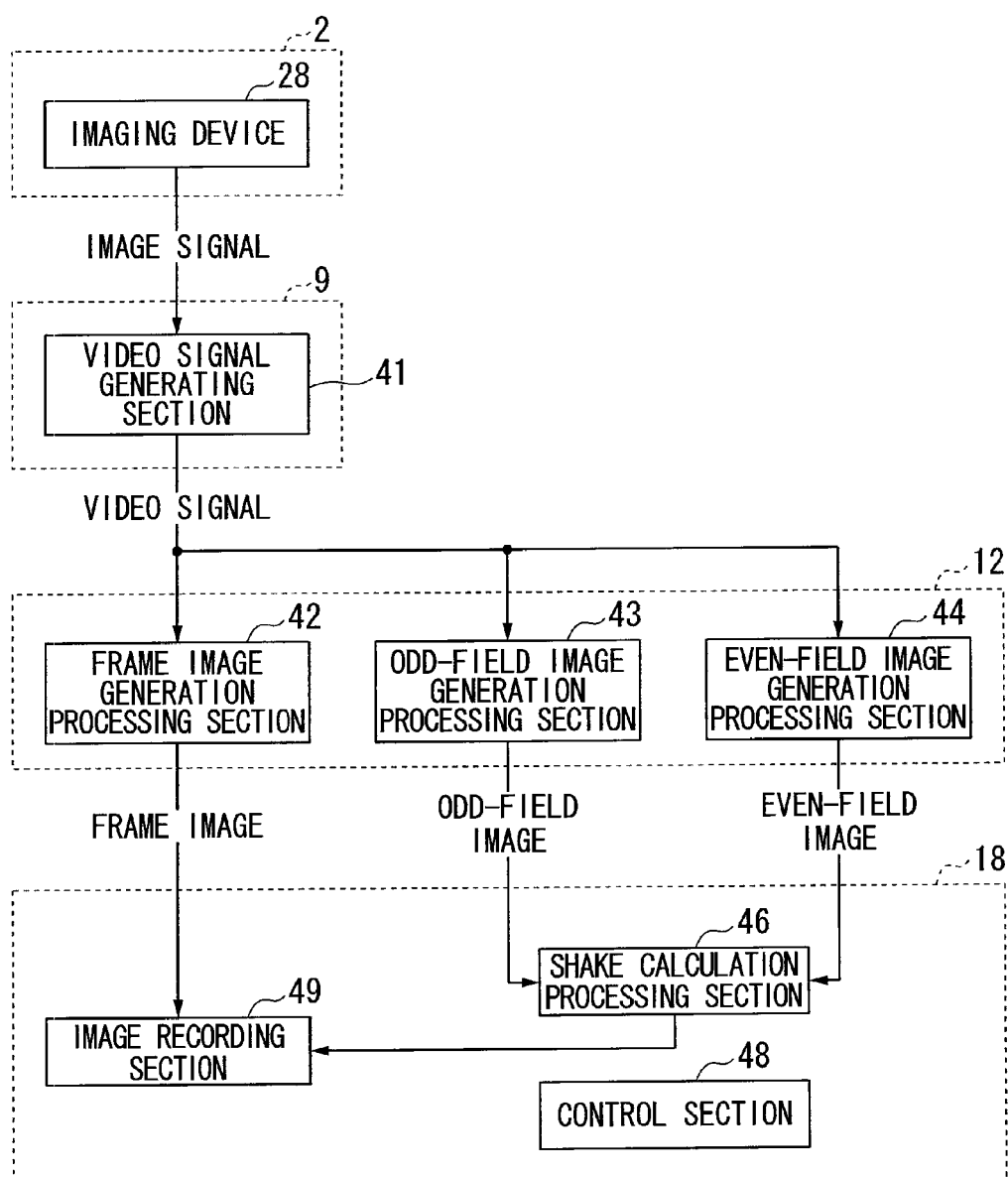
FIG. 4 is a block diagram representing the functional configuration of an endoscope apparatus according to an embodiment of the present invention.
Figure 5:
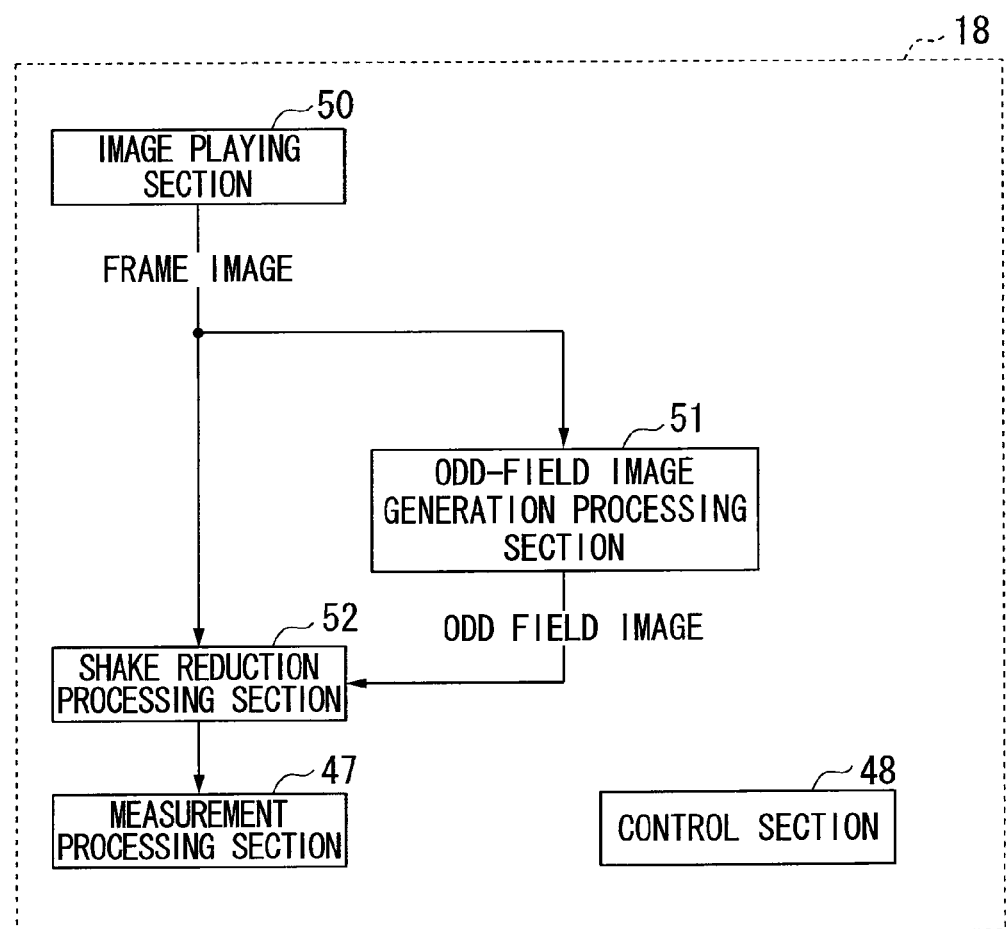
FIG. 5 is a block diagram representing the functional configuration of an endoscope apparatus according to an embodiment of the present invention.

FIGS. 3, 4, and 5 represent the functional configurations of portions of the endoscope apparatus 1 that are focused in description of this embodiment. FIG. 3 represents the functional configuration for a case where an operation for starting a measurement mode is performed. FIG. 4 represents the functional configuration for a case where an operation for image recording is performed. The operation for image recording is an operation of inputting a direction for recording a frame image into the memory card 32 or the like. FIG. 5 represents the functional configuration for a case where an operation for starting a play mode is performed. The operation for starting a play mode is an operation of inputting a direction for playing the frame image that is stored in the memory card 32 or the like by the operation for image recording.

A video signal generating section 41 corresponds to the function of the CCU 9. This video signal generating section 41 generates a video signal that configures a first image based on the image signal that is output from the imaging device 28.

In particular, the video signal generating section 41 alternately outputs a video signal of an odd field and a video signal of an even field in synchronization with the interlaced driving of the imaging device 28.

A frame image generation processing section 42, an odd-field image generation processing section 43, and an even-field image generation processing section 44 correspond to the function of the video signal processing circuit 12. The frame image generation processing section 42 generates a frame video signal by synthesizing the video signal of the odd field and the video signal of the even field that are output from the video signal generating section 41. Hereinafter, the frame video signal that is generated by the frame image generation processing section 42 is referred to as a frame image. A video signal of an odd row (odd field) of a frame image is configured by a video signal of an odd field that is output from the video signal generating section 41. On the other hand, a video signal of an even row (even field) of a frame image is configured by a video signal of an even field that is output from the video signal generating section 41.

The odd-field image generation processing section 43 generates a frame video signal based on a video signal of an odd field that is output from the video signal generating section 41. Hereinafter, a frame video signal that is generated by the odd-field image generation processing section 43 is referred to as an odd-field image. A video signal of an odd row (odd field) of the odd-field image is configured by a video signal of an odd field that is output from the video signal generating section 41. On the other hand, a video signal of an even row (even field) of the odd-field image is interpolated by video signals of an odd row. A video signal of each even row of an odd-field image may be an average of video signals of odd rows that are vertically adjacent thereto.

The even-field image generation processing section 44 generates a frame video signal based on a video signal of an even field that is output from the video signal generating section 41. Hereinafter, a frame video signal that is generated by the even-field image generation processing section 44 is referred to as an even-field image. A video signal of an even row (even field) of the even-field image is configured by a video signal of an even field that is output from the video signal generating section 41. On the other hand, a video signal of an odd row (odd field) of the even-field image is interpolated by video signals of an even row. A video signal of each odd row of the even-field image may be an average of video signals of even rows that are vertically adjacent thereto.

In addition, shake reduction processing sections 45 and 52, a shake calculation processing section 46, a measurement processing section 47, a control section 48, an image recording section 49, an image playing section 50, and an odd-field image generation processing section 51 correspond to the function of the CPU 18. The shake calculation processing section 46 calculates a motion vector, which is a motion parameter between images, based on the odd-field image output from the odd-field image generation processing section 43 and the even-field image output from the even-field image generation processing section 44. When the magnitude of the motion vector that is calculated by the shake calculation processing section 46 exceeds a predetermined value, the shake reduction processing section 45 performs a process of substituting the frame image output from the frame image generation processing section 42 with the odd-field image (second image) output from the odd-field image generation processing section 43. Alternatively, the even-field image may be configured to be used instead of the odd-field image.

The imaging device 28 performs scanning twice, the first time for odd rows and the second time for even rows by the interlaced driving. Accordingly, in a frame image, when there is a motion of the distal end portion 21 or an observation target, shake occurs in the image due to a difference in timings for performing scanning twice. On the other hand, since being configured by a video signal of an odd field that is acquired by scanning once, the odd-field image has shake less than the frame image even in a case where there is a motion of the distal end portion 21 or the observation target.

The measurement processing section 47 performs a measurement process based on the frame image or the odd-field image. The control section 48 controls assigning of processes to each section such as the shake reduction processing section 45 and controls the overall operation of the endoscope apparatus 1.

When an operation for image recording is performed, the image recording section 49 records the frame image that is generated by the frame image generation processing section 42 and a shake detection flag in the memory card 32 or the like. The shake detection flag is a flag that contains a value corresponding to the magnitude of the motion vector calculated by the shake calculation processing section 46. When an operation for starting a play mode is performed, the image playing section 50 plays the frame image and the shake detection flag that are recorded in the memory card 32 or the like.

The odd-field image generation processing section 51 generates a frame video signal based on video signals of odd rows within the frame image that is played by the image playing section 50. Hereinafter, a frame video signal that is generated by the odd-field image generation processing section 51 is referred to as an odd-field image. The video signal of an odd row (odd field) of the odd-field image is configured by video signals of odd rows within the frame image that is played by the image playing section 50. The video signal of an even row (even field) of the odd-field image is interpolated with video signals of odd rows. The video signal of each even row of the odd-field image may be an average of video signals of odd rows that are vertically adjacent thereto.

In a case where the value of the shake detection flag that is played by the image playing section 50 is a predetermined value, the shake reduction processing section 52 performs a process of substituting the frame image, which is played by the image playing section 50, with the odd-field image (second image) that is generated by the odd-field image generating section 51. A case where the shake detection flag is a predetermined value corresponds to a case where the magnitude of the motion vector calculated before recording by the shake calculation processing section 46 exceeds a predetermined value.

Figure 6:
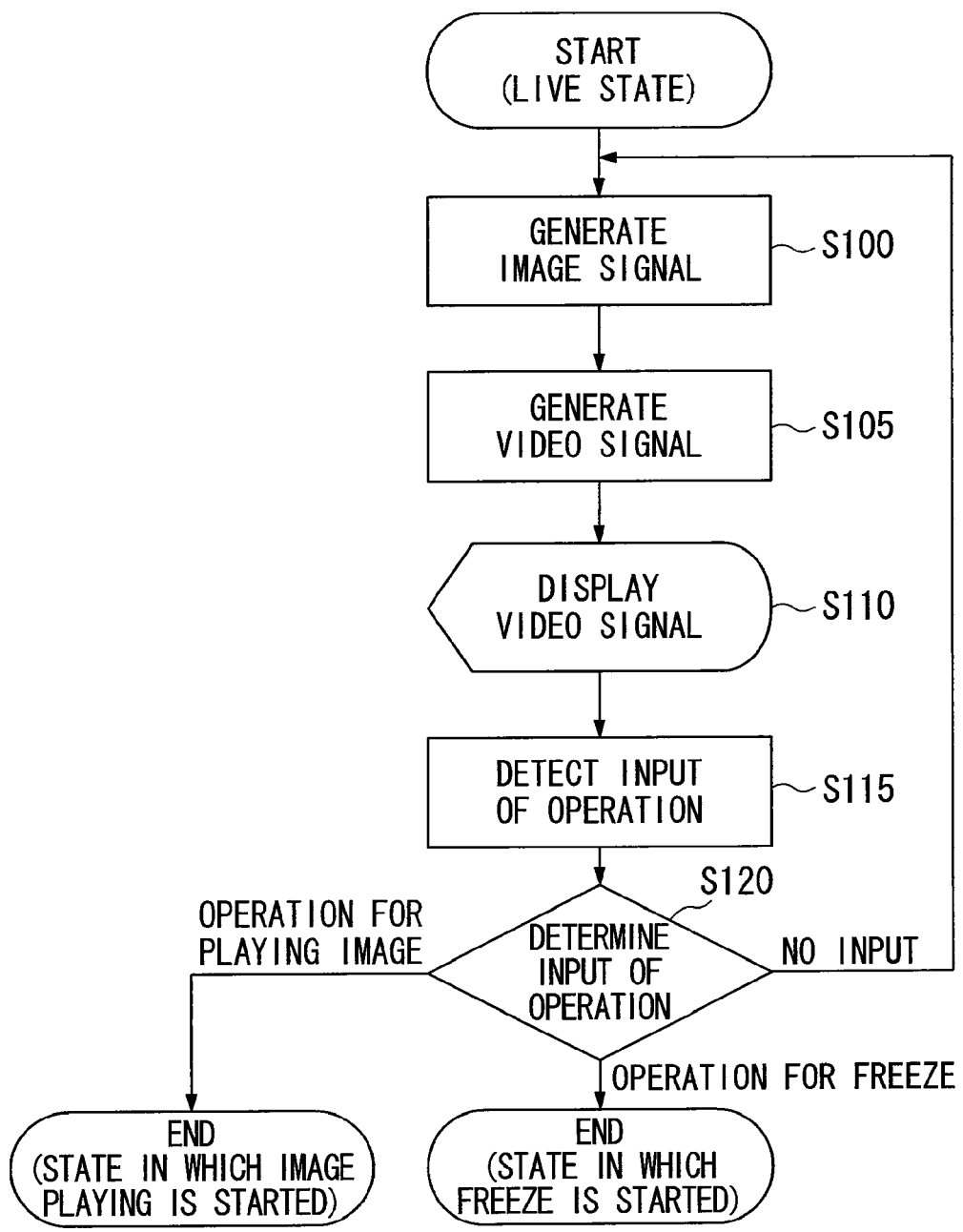
FIG. 6 is a flowchart representing the operation flow of an endoscope apparatus according to an embodiment of the present invention.

Next, the operation of the endoscope apparatus 1 according to this embodiment will be described. When the power is turned on, the mode of the endoscope apparatus 1 is a live mode in which an imaging operation and an image displaying operation are performed in an alternating manner. As represented in FIG. 6, in the live mode, the imaging device 28 generates an odd-field image signal and an even-field image signal by performing scanning operations for the odd rows and the even rows (Step S100). The video signal generating section 41 converts the odd-field image signal and the even-field image signal into video signals and outputs an odd-field video signal and an even-field video signal (Step S105).

The video signal processing circuit 12 generates a display signal by synthesizing a graphic image signal supplied from the CPU 18, the even-field video signal, and the odd-field video signal and outputs the display signal to the monitor 4. The monitor 4 displays an image based on the display signal (Step S110). The control section 48 detects a signal from the operation portion 6 (Step S115) and determines the type of the user's operation for the operation portion 6 (Step S120). When the user does not perform any operation, the process returns to Step S100. On the other hand, when the user performs a freeze operation, the endoscope apparatus 1 is in a state in which freeze is started.

The freeze operation (a first operation direction) is an operation of inputting a direction for displaying a still image.

On the other hand, when the user performs the operation for starting the play mode, the endoscope apparatus 1 is in a state in which image playing is started.

Figure 7:
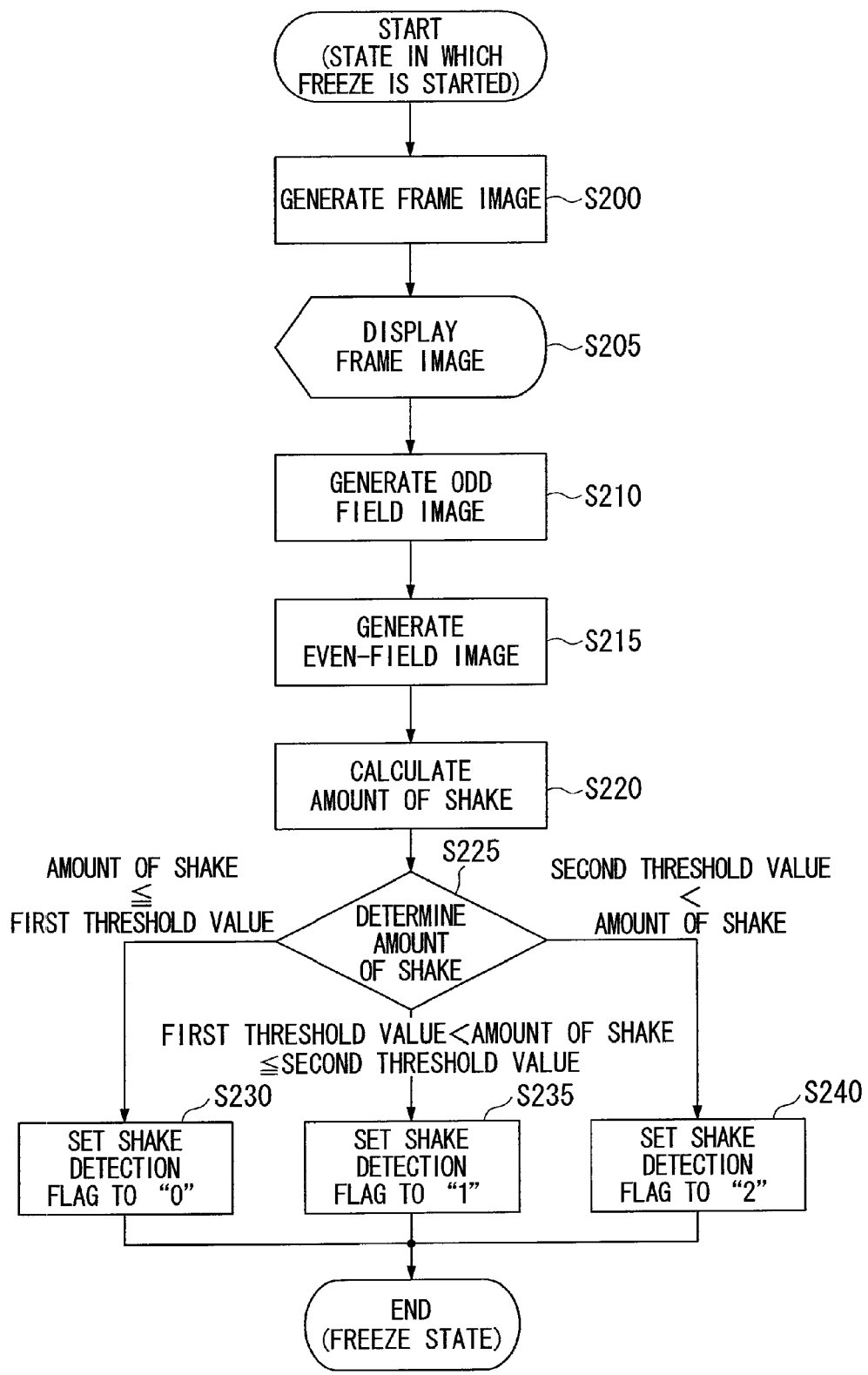
FIG. 7 is a flowchart representing the operation flow of an endoscope apparatus according to an embodiment of the present invention.

As represented in FIG. 7, in a state in which the freeze is started, the frame image generation processing section 42 generates a frame image by synthesizing the odd-field video signal and the even-field video signal that are output from the video signal generating section 41 (Step S200). The video signal processing circuit 12 generates a display signal by synthesizing the graphic image signal that is supplied from the CPU 18 and the frame image and outputs the display signal to the monitor 4. The monitor 4 displays an image based on the display signal (Step S205). The image displayed on the monitor 4 is a still image, and the monitor 4 continues to display the still image until the freeze state is over.

Thereafter, the odd-field image generation processing section 43 generates an odd-field image based on the odd-field video signal that is output from the video signal generating section 41 (Step S210). In addition, the even-field image generation processing section 44 generates an even-field image based on the even-field video signal output from the video signal generating section 41 (Step S215).

Alternatively, the generating of the odd-field image and the even-field image may be performed before the generating of the frame image.

Thereafter, the shake calculation processing section 46 calculates a motion vector, which becomes an index of the amount of shake occurring in the frame image, based on the odd-field image output from the odd-field image generation processing section 43 and the even-field image output from the even-field image generation processing section 44 (Step S220). Hereinafter, a method of calculating the motion vector will be described.

In this embodiment, when measurement is performed, left and right subject images (hereinafter, referred to as a left-side image and a right-side image) forming one pair are imaged by a stereo optical adapter that can locate two subject images for one subject. Accordingly, a left-side image and a right-side image are respectively included in images corresponding to a frame image, an odd-field image, and an even-field image.

The shake calculation processing section 46, for example, sets the range of W×H pixels, which is acquired by using a center point of a left-side image included in the odd-field image as its center, as a template and searches for a corresponding point on the even-field image that corresponds to the center point. The searching for the corresponding point, for example, is performed by calculating SAD (Sum of Absolute Differences) of the luminance levels. In a case where the pixel value of the template is denoted by t(x,y) and the pixel value of a search target image is denoted by g(x,y), generally, F(u,v), which is the SAD in the coordinates (u,v), can be acquired by using Equation (1).

Equation (1)

$$F(u, v) = \sum_{i \in N_W} \sum_{j \in N_R} |g(i+u, j+v) - t(i, j)| \quad (1)$$

Here, the width of the template is denoted by W, and the height of the template is denoted by H, wherein $-W/2 \leq N_w \leq W/2$ and $-H/2 \leq N_H \leq H/2$. In addition, center coordinates of the left-side image included in an image corresponding to an odd-field image are denoted by (Ox,Oy), and F(u,v) is calculated in the range of $Ox-W/2 \leq u \leq Ox+W/2$ and $Oy-H/2 \leq v \leq Oy+H/2$. Here, coordinates (Ex,Ey) for a case where F(u,v) is the minimum correspond to the corresponding point.

The motion vector m can be calculated from the coordinates (Ex,Ey) of the corresponding point of the center coordinates (Ox,Oy) of the left-side image included in the odd-field image by using Equation (2).

$$m=(Ex-Ox, Ey-Oy) \quad \text{Equation (2)}$$

The method of calculating the motion vector is as described above.

When the calculation of the motion vector is completed, the control section 48 determines the magnitude relationship between two threshold values set in advance and the magnitude of the motion vector (Step S225). Hereinafter, the two threshold values are referred to as the first threshold value and the second threshold value, wherein the relationship of "first threshold value<second threshold value" is satisfied. When the magnitude of the motion vector is equal to or less than the first threshold value, the control section 48 sets "0" to the shake detection flag (Step S230). On the other hand, when the magnitude of the motion vector exceeds the first threshold value and is less than the second threshold value, the control section 48 sets "1" to the shake detection flag (Step S235).

In addition, when the magnitude of the motion vector exceeds the second threshold value, the control section 48 sets "2" to the shake detection flag (Step S240). When the processes of Steps S230, S235, and S240 are completed, the endoscope apparatus 1 is in the freeze state.

Figure 8:
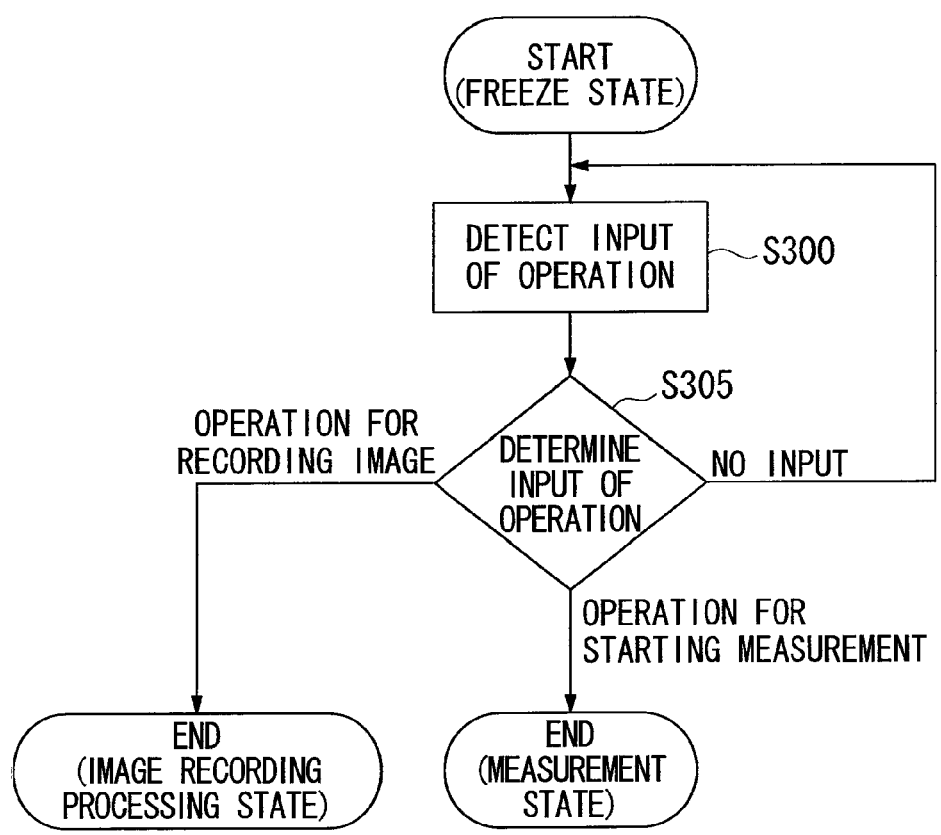
FIG. 8 is a flowchart representing the operation flow of an endoscope apparatus according to an embodiment of the present invention.

In the freeze state, as represented in FIG. 8, the control section 48 detects a signal transmitted from the operation portion 6 (Step S300) and determines the type of the user's operation for the operation portion 6 (Step S305). In a case where the user does not perform any operation, the process returns back to Step S300. On the other hand, in a case where the user performs the operation (direction for the second operation) for starting the measurement mode, the mode of the endoscope apparatus 1 becomes the measurement mode. In addition, when the user performs an operation for image recording, the endoscope apparatus 1 is in the state in which an image is recorded.

Figure 9:
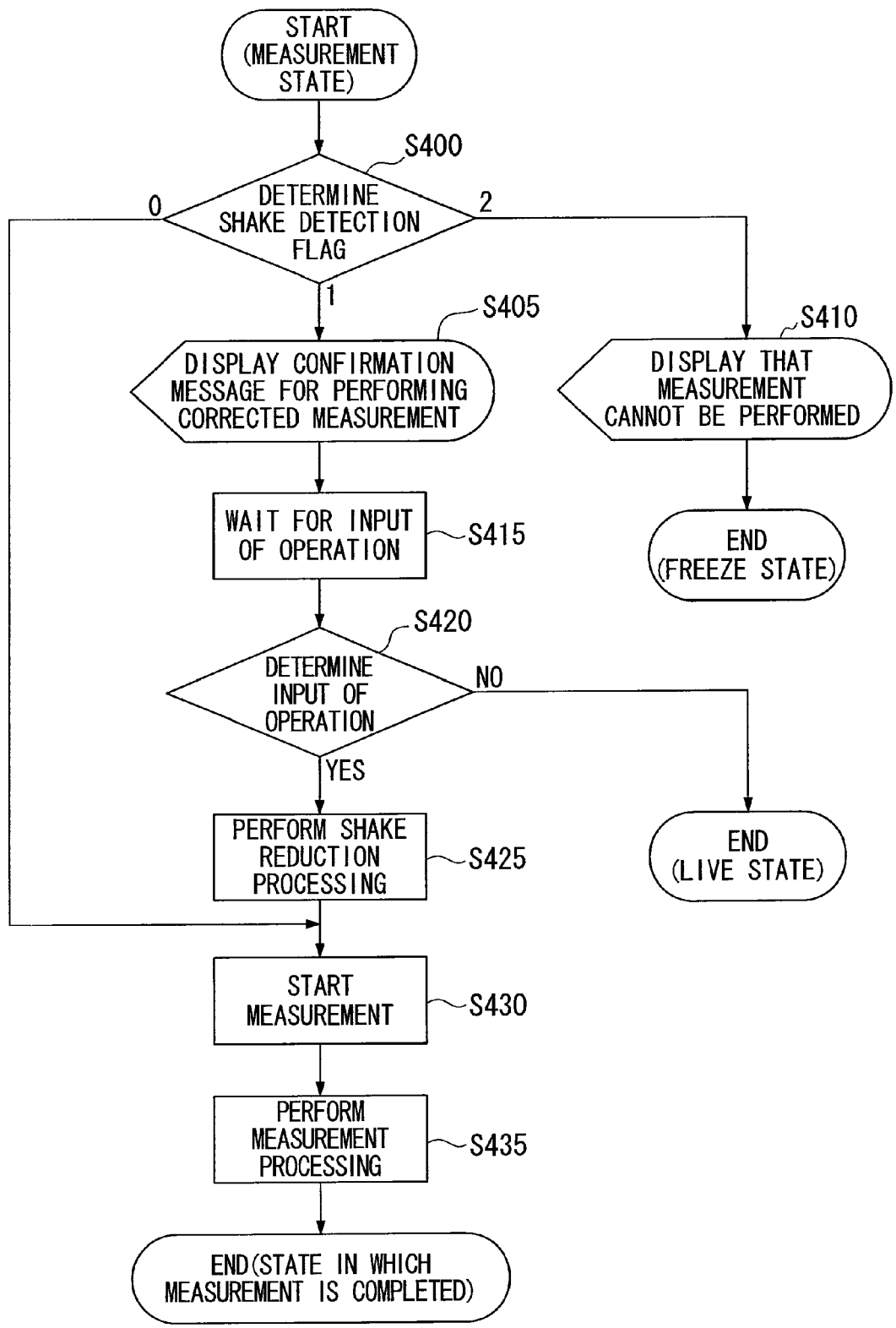
FIG. 9 is a flowchart representing the operation flow of an endoscope apparatus according to an embodiment of the present invention.

In the measurement mode, as represented in FIG. 9, the control section 48 determines the value of the shake detection flag set in Steps S230, S235, and S240 (Step S400). When the value of the shake detection flag is "0", the process proceeds to Step S430. In such a case, the frame image is used in the measurement process performed thereafter. On the other hand, when the value of the shake detection flag is "1", the process proceeds to Step S405. In such a case, the odd-field image, which has an amount of shake less than the frame image, is used in the measurement process performed thereafter.

In addition, when the value of the shake detection flag is "2", the video signal processing circuit 12 generates a display signal by synthesizing the graphic image signal that is supplied from the CPU 18 and the frame image and outputs the display signal to the monitor 4. At this moment, the graphic image signal that is supplied from the CPU 18 includes a warning message that is used for notifying the user that the measurement cannot be performed and the like. The monitor 4 displays an image based on the display signal. Accordingly, the warning message and the like are displayed on the monitor 4 together with the endoscopic image (Step S410). In such a case, since the control section 48 does not start the measurement processing section 47, the measurement process is not performed. In Step S410, a warning message may be displayed on the monitor 4, or the value of the amount of shake may be displayed on the monitor. Accordingly, the user can notice whether the frame image is appropriate for measurement before performing the measurement.

When the process proceeds to Step S405, the video signal processing circuit 12 generates a display signal by synthesizing the graphic image signal supplied from the CPU 18 and the frame image and outputs the display signal to the monitor 4. The graphic image signal supplied from the CPU 18 at this moment includes a confirmation message and the like for allowing the user to select whether or not to perform measurement after correction of the video signal. The monitor 4 displays an image based on the display signal. Accordingly, a confirmation message or the like is displayed on the monitor 4 together with the endoscopic image (Step S405).

Thereafter, the control section 48 waits a user's operation by monitoring a signal transmitted from the operation portion 6 (Step S415). When the user performs an operation, the control section 48 determines the type of the user's operation for the operation portion 6 (Step S420). When the user operates to reject to perform measurement after correction of the video signal, the mode of the endoscope apparatus 1 returns to the live mode. In such a case, since the control section 48 does not start the measurement processing section 47, the measurement process is not performed. On the other hand, when the user performs an operation to permit to perform the measurement after correction of the video signal, the shake reduction processing section 45 performs a process of substituting the frame image output from the frame image generation processing section 42 with the odd-field image that is output from the odd-field image generation processing section 43 (Step S425).

Thereafter, the control section 48 starts the measurement processing section 47. In addition, the video signal processing circuit 12 generates a display signal by synthesizing the graphic image signal supplied from the CPU 18 and the odd-field image and outputs the display signal to the monitor 4. The graphic image signal supplied from the CPU 18 at this moment includes a menu relating to the measurement and the like. Accordingly, a measurement menu and the like are displayed on the monitor 4 together with the endoscopic image (Step S430). Thereafter, the measurement processing section 47 performs a measurement process based on the frame image or the odd-field image (Step S435).

When the value of the shake detection flag is "0", the frame image that is generated in Step S200 is used for the measurement process. On the other hand, when the value of the shake detection flag is "1", the odd-field image replacing the frame image in Step S425 is used for the measurement process.

In the measurement process that is performed in Step S435, a process of setting a measurement point on the endoscopic image based on the type of the user's operation for the operation portion 6, a process of calculating a length or an area that is designated in the measurement point, and the like are included. In this measurement process, an image on the basis of the frame image or the odd-field image is displayed on the monitor 4, and the measurement point is set on the image.

Figure 15:
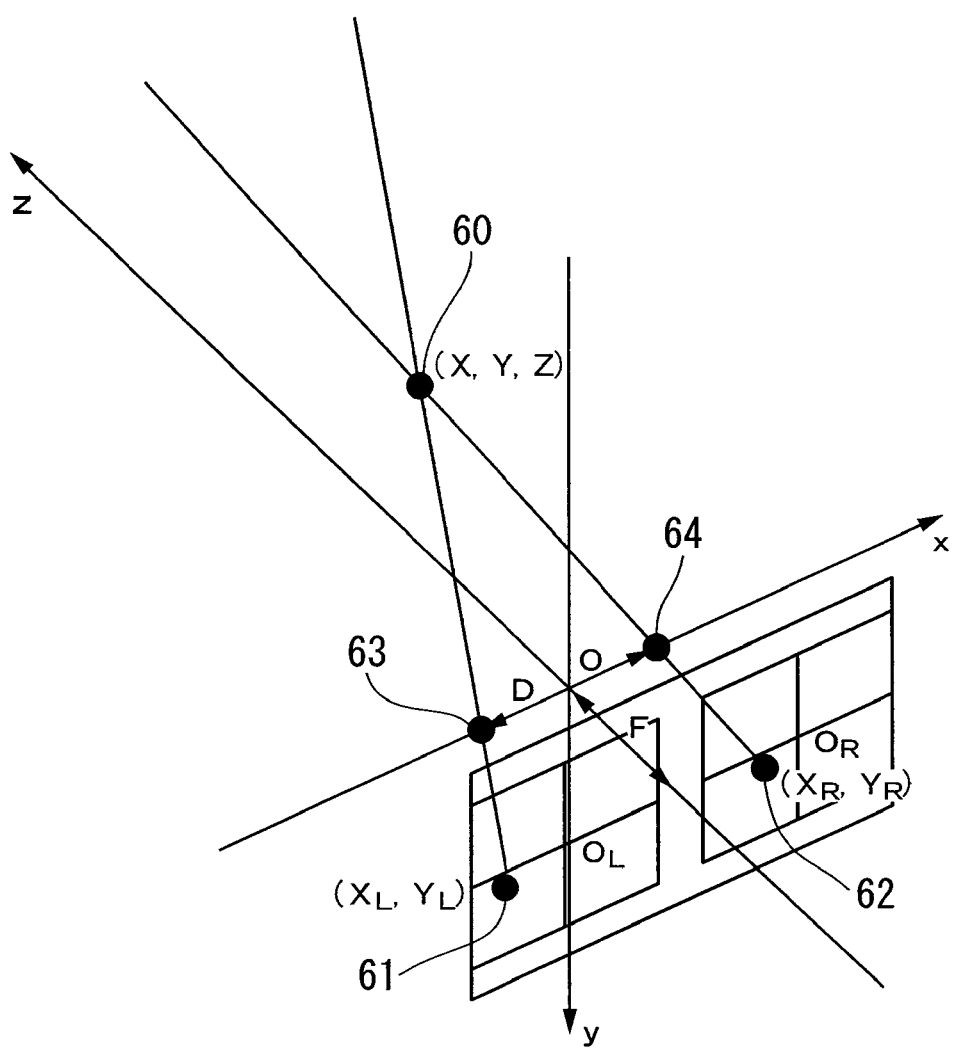
FIG. 15 is a reference diagram for describing a method of acquiring three-dimensional coordinates of a measurement point by performing stereo measurement.

In addition, in the measurement process that is performed in Step S435, three-dimensional coordinates of the measurement point located in spot coordinates are calculated by performing stereo measurement using the principle of triangulation and are used for calculating length or area. Hereinafter, a method of calculating three-dimensional coordinates of the measurement point by using the stereo measurement will be described with reference to FIG. 15. For an image that is imaged by using left-side and right-side optical systems, three-dimensional coordinates (X,Y,Z) of the measurement point 60 are calculated by using the triangulation method by the following Equations (3) to (5). Here, the coordinates of measurement points 61 and 62 located on the left-side and right-side images, for which distortion correction has been made, are denoted by $(X_L, Y_L)$ and $(X_R, Y_R)$, a distance between right-side and left-side optical centers 63 and 64 is denoted by D, and the focal distance is denoted by F, wherein $t = D/(X_L - X_R)$.

$$X = t \times X_R + D/2 \qquad \text{Equation (3)}$$

$$Y = t \times Y_R \qquad \text{Equation (4)}$$

$$Z = t \times F \qquad \text{Equation (5)}$$

As described above, when the coordinates of the measurement points 61 and 62 located on the original image are determined, the three-dimensional coordinates of the measurement point 60 are acquired by using parameters D and F. By acquiring the three-dimensional coordinates of several points, various measurements such as a distance between two points, a distance between a line joining two points and one point, an area, a depth, and a surface shape can be performed. In addition, a distance (object distance) between a left-side optical center 63 or a right-side optical center 64 and a subject also can be acquired. In order to perform the above-described stereo measurement, optical data representing the characteristics of the optical system including the distal end portion 21 of the endoscope and the stereo optical adapter is needed. In addition, a detailed description of the optical data, for example, is disclosed in Japanese Patent Application Laid-Open Publication No. 2004-49638. Thus, a detailed description thereof is omitted here.

Figure 10:
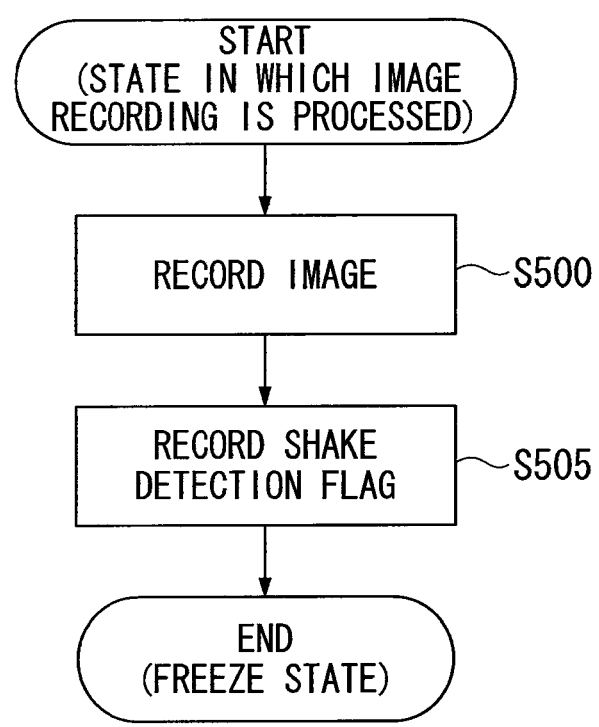
FIG. 10 is a flowchart representing the operation flow of an endoscope apparatus according to an embodiment of the present invention.

In the state in which an image is recorded, as shown in FIG. 10, the image recording section 49 records the frame image generated in Step S200 in the memory card 32 or the like (Step S500). In addition, the image recording section 49 records the shake detection flag set in Steps S230, S235, and S240 in the memory card 32 or the like (Step S505). When the process of Step S505 is completed, the endoscope apparatus 1 is in the freeze state.

Figure 11:
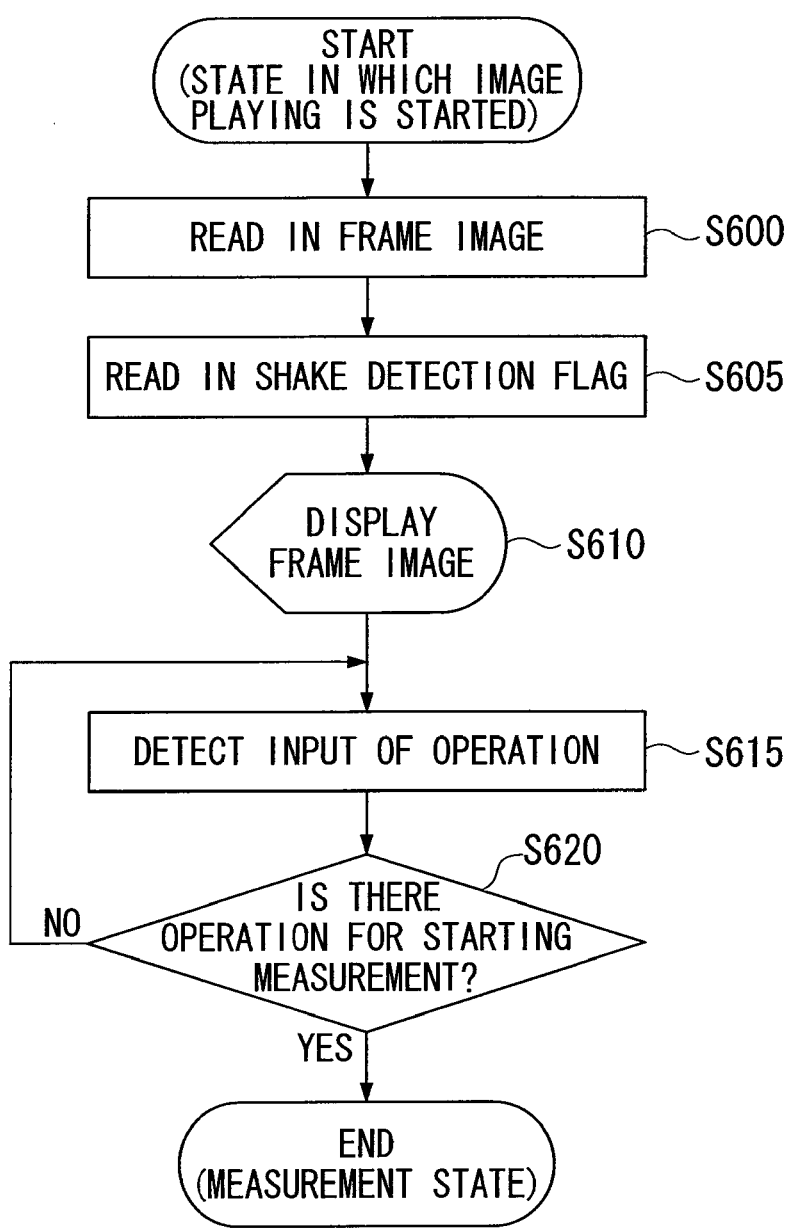
FIG. 11 is a flowchart representing the operation flow of an endoscope apparatus according to an embodiment of the present invention.

In the state in which an image is played, as shown in FIG. 11, the image playing section 50 reads in the frame image from the memory card 32 or the like (Step S600). In addition, the image playing section 50 reads in the shake detection flag from the memory card 32 or the like (Step S605). The video signal processing circuit 12 generates a display signal by synthesizing the graphic image signal supplied from the CPU 18 and the frame image and outputs the display signal to the monitor 4. The monitor 4 displays an image based on the display signal (Step S610).

Thereafter, the control section 48 determines whether the user performs an operation to start the measurement mode (Step S620) by detecting a signal transmitted from the operation portion 6 (Step S615). When the user does not perform the operation to start the measurement mode, the process returns back to Step S615. On the other hand, when the user operates to start the measurement mode, the mode of the endoscope apparatus 1 becomes the measurement mode.

Figure 12:
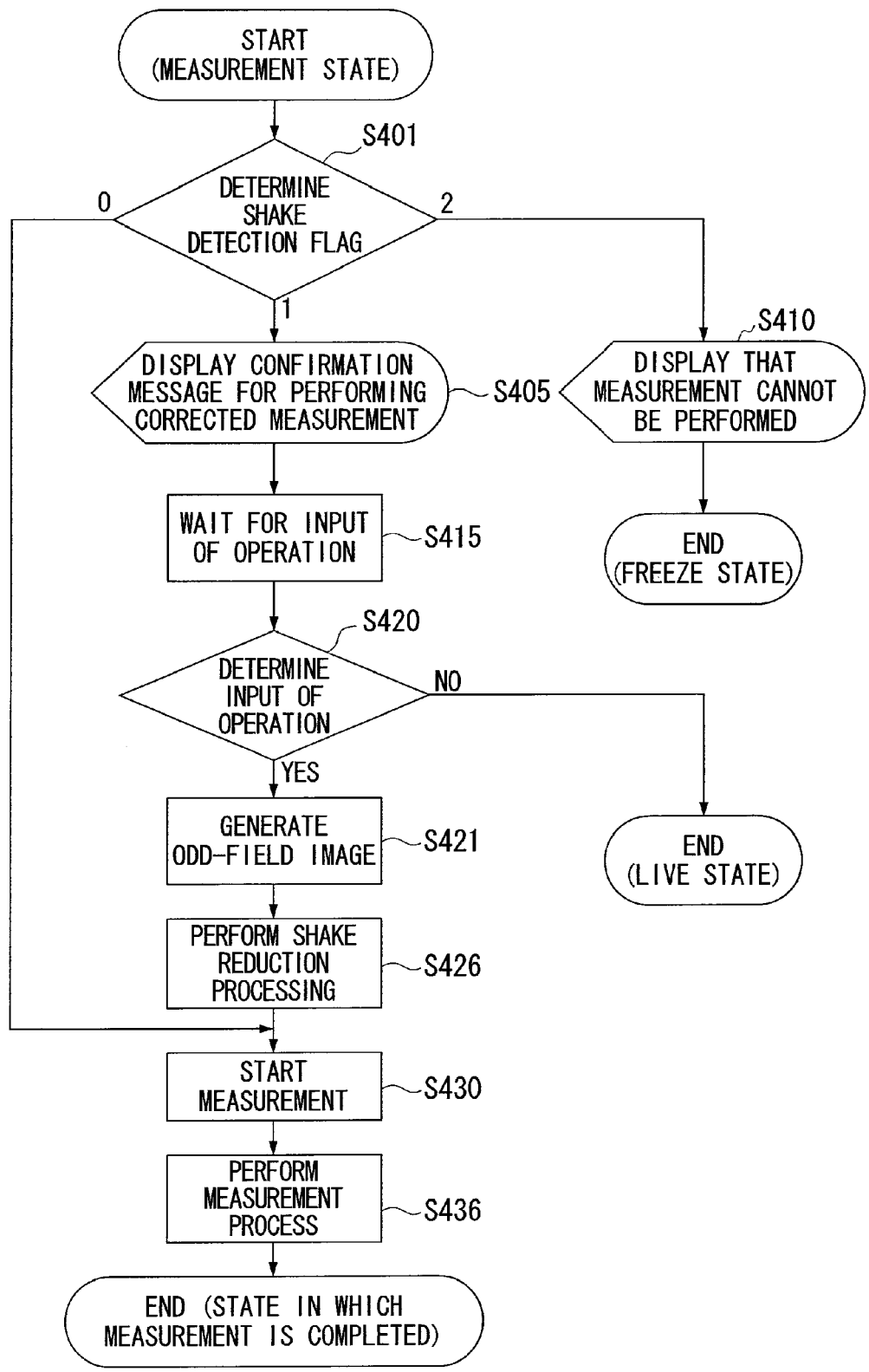
FIG. 12 is a flowchart representing the operation flow of an endoscope apparatus according to an embodiment of the present invention.

In the measurement mode, the process represented in FIG. 12 is performed. In FIG. 12, a same step number is assigned to each process that is the same as that represented in FIG. 9. In FIG. 12, a process of Step S421 that is not included in the process represented in FIG. 9 is added. In addition, in FIG. 12, although the contents of the processes of Steps S401, S426, and S436 are the same as those of Steps S400, S425, and S435 represented in FIG. 9, data or signals used for the processes are different from those used in the processes of Steps represented in FIG. 9.

In Step S401, the value of the shake detection flag read from the memory card 32 or the like in Step S605 is used. The branching of the process performed in accordance with the value of the shake detection flag is as represented in FIG. 9. In Step S421, the odd-field image generation processing section 51 generates an odd-field image based on the video signals of odd rows within the frame image that is read from the memory card or the like in Step S600. In Step S426, the shake reduction processing section 45 substitutes the frame image read from the memory card or the like in Step S600 with the odd-field image generated in Step S421.

In Step S436, when the value of the shake detection flag is "0", the frame image read from the memory card or the like in Step S600 is used for the measurement process. On the other hand, in Step S436, when the value of the shake detection flag is "1", the odd-field image substituting the frame image in Step S426 is used for the measurement process.

Figure 13:
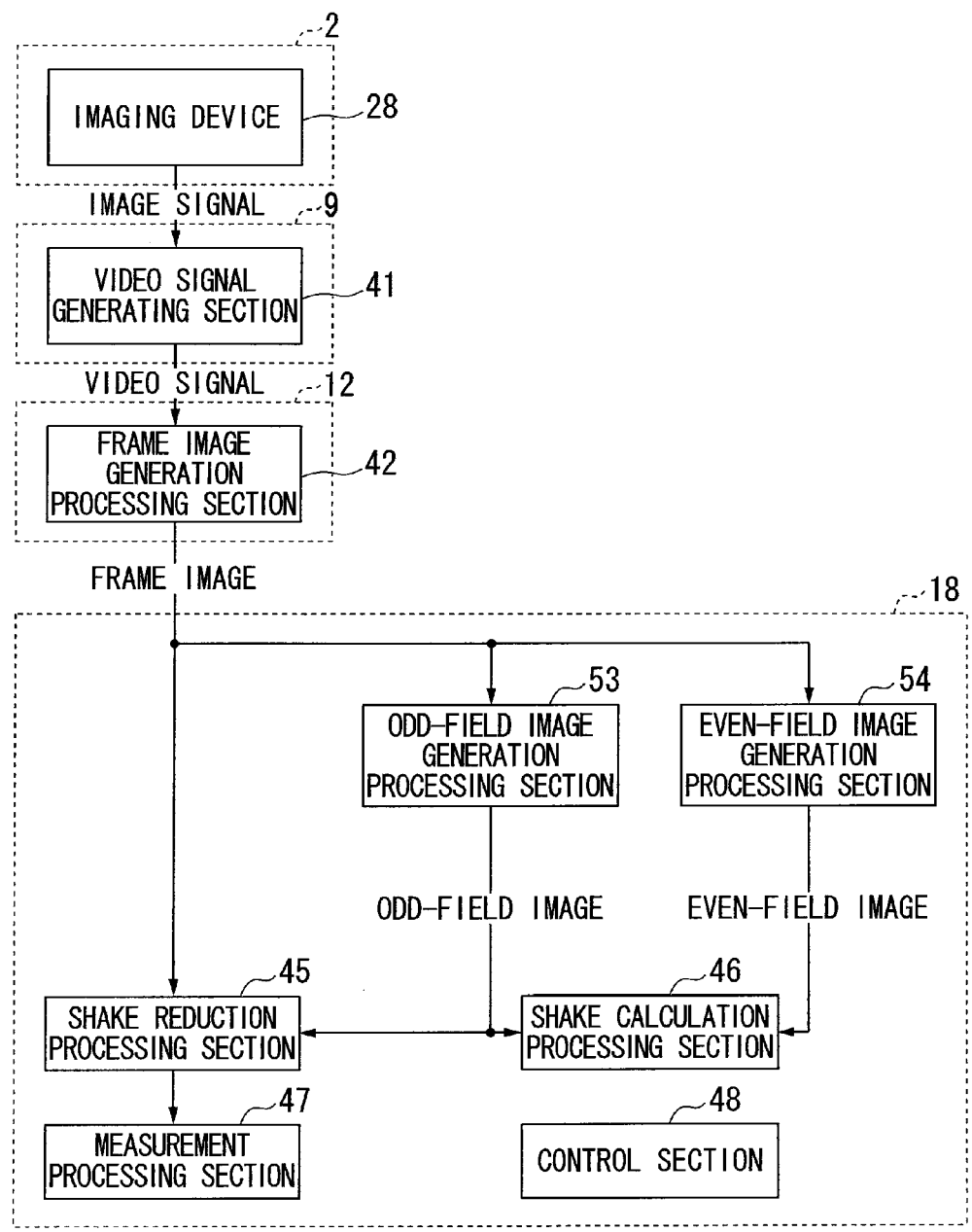
FIG. 13 is a block diagram representing the functional configuration of an endoscope apparatus according to an embodiment of the present invention.

Next, modified examples of this embodiment will be described. FIG. 13 is a modified example of the functional configuration represented in FIG. 3. In FIG. 3, the odd-field image generation processing section 43 and the even-field image generation processing section 44 corresponding to the function of the video signal processing circuit 12 are disposed. However, an odd-field image generation processing section 53 and an even-field image generation processing section 54 corresponding to the function of the CPU 18 are disposed in FIG. 13, instead of the odd-field image generation processing section 43 and the even-field image generation processing section 44.

The odd-field image generation processing section 53 generates a frame video signal based on the frame image that is output from the frame image generation processing section 42. Hereinafter, the frame video signal that is generated by the odd-field image generation processing section 53 is referred to as an odd-field image. The video signal of an odd row (odd field) of the odd-field image is configured by video signals of odd rows within the frame image that is output from the frame image generation processing section 42. The video signal of an even row (even field) of the odd-field image is interpolated with the video signals of odd rows. The video signal of each even row of the odd-field image may be an average of video signals of odd rows that are vertically adjacent thereto.

The even-field image generation processing section 54 generates a frame video signal based on the frame image that is output from the frame image generation processing section 42. Hereinafter, the frame video signal that is generated by the even-field image generation processing section 54 is referred to as an even-field image. The video signal of an even row (even field) of the even-field image is configured by video signals of even rows within the frame image that is output from the frame image generation processing section 42. The video signal of an odd row (odd field) of the even-field image is interpolated with the video signals of even rows. The video signal of each odd row of the even-field image may be an average of video signals of even rows that are vertically adjacent thereto.

The shake calculation processing section 46 calculates a motion vector based on the odd-field image generated by the odd-field image generation processing section 53 and the even-field image generated by the even-field image generation processing section 54. When the magnitude of the motion vector that is calculated by the shake calculation processing section 46 exceeds a predetermined value, the shake reduction processing section 45 substitutes the frame image output from the frame image generation processing section 42 with the odd-field image (second image) that is generated by the odd-field image generation processing section 53. Alternatively, the even-field image may be used instead of the odd-field image.

The operation of the endoscope apparatus 1 having the functional configuration represented in FIG. 13 is the same as that described with reference to FIGS. 6 to 12.

Figure 14:
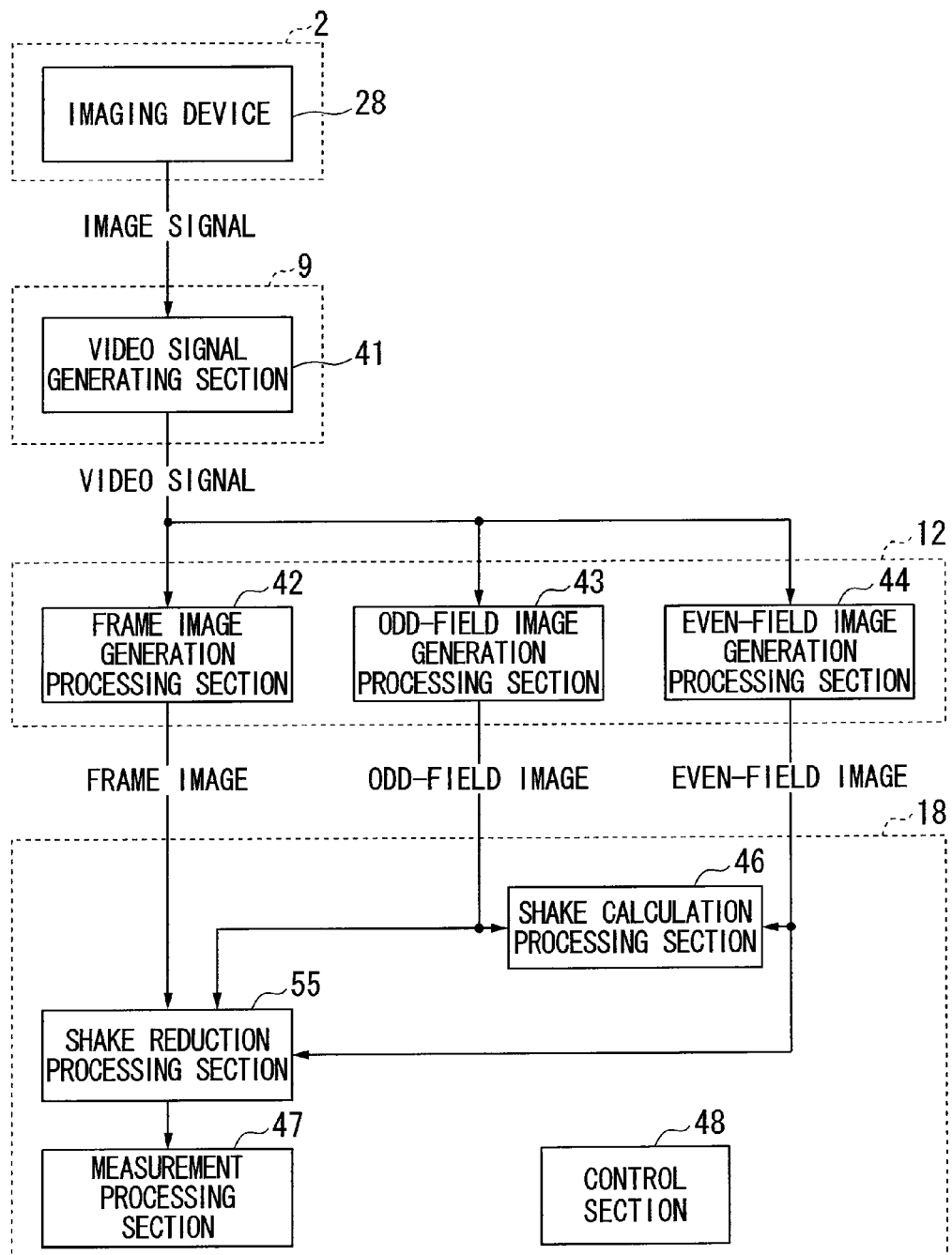
FIG. 14 is a block diagram representing the functional configuration of an endoscope apparatus according to an embodiment of the present invention.

FIG. 14 is another modified example of the functional configuration represented in FIG. 3. In FIG. 14, the process performed by a shake reduction processing section 55 corresponding to the function of the CPU 18 is different from that performed by the shake reduction processing section 45 represented in FIG. 3.

When the magnitude of the motion vector that is calculated by the shake calculation processing section 46 exceeds a predetermined value, the shake reduction processing section 55 generates video signals acquired by correcting at least one of video signals of even-rows and video signals of odd rows, which configure the frame image output from the frame image generation processing section 42, based on the motion vector. Hereinafter, the video signal that is generated by the shake reduction processing section 55 is referred to as a corrected frame image (second image). In particular, the shake reduction processing section 55 generates the corrected frame image in the following manner.

Here, the luminance of the pixel(i,j) of the odd-field image is denoted by $f1(i,j)$, the luminance of the pixel(i,j) of the even-field image is denoted by $f2(i,j)$, and the luminance of the pixel(i,j) of the corrected image is denoted by $f3(i,j)$. In addition, the motion vector m, which is calculated by the shake calculation processing section 46, is calculated by using the following Equation (6).

$$m=(Ex-Ox,Ey-Oy)=(Mx,My) \quad \text{Equation (6)}$$

The shake reduction processing section 55 generates corrected images by using the following Equations (7) and (8).

$$f3(i,j)=f1(i,j) \text{(when } j \text{ is an odd number)} \quad \text{Equation (7)}$$

$$f3(i,j)=f2(i+Mx,j+My) \text{(when } j \text{ is an even number)} \quad \text{Equation (8)}$$

In the above-described case, the shake reduction processing section 55 generates corrected frame images acquired by correcting the video signals of even rows of the frame image. However, the shake reduction processing section 55 may be configured to generate corrected frame images acquired by correcting video signals of odd rows of the frame image or to generate corrected frame images acquired by correcting video signals of even and odd rows of the frame image. In addition, in Equation (8), when the pixel (i+Mx, j+My) is out of the range of pixels that constitute the even-field image, it is set that $f3(i,j)=f2(i,j)$, and an image acquired by excluding the outer periphery portion from the corrected frame image that is finally generated may be used in processes performed thereafter.

The operation of the endoscope apparatus 1 having the functional configuration represented in FIG. 14 is the same as that described with reference to FIGS. 6 to 12. However, in Step S425, the shake reduction processing section 55 generates the corrected frame image as described above. In addition, in Step S435, when the value of the shake detection flag is "1", the measurement processing section 47 performs the measurement process by using the corrected frame image.

In addition, in Step S426, the shake reduction processing section 52 represented in FIG. 5 operates. However, in the functional configuration represented in FIG. 5, it may be configured that an even-field image generation processing section, which generates an even-field image from the frame image played by the image playing section 50, is added, and a shake reduction processing section, which generates a corrected frame image from the even-field image and the odd-field image, is disposed instead of the shake reduction processing section 52.

As motion parameters according to this embodiment, the amount of rotation and an enlargement factor other than the motion vector may be needed. The amount of rotation is acquired based on a difference in the slopes of principal axes of inertia of the even-field image and the odd-field image. When the luminance of the pixel(i,j) of the odd-field image is denoted by f(i,j), the second-order moment of the odd-field image can be acquired by using the following Equations (9) to (11).

Equation (9)
$$m_{20} = \sum_{i \in N_n} i^2 \sum_{j \in N_m} f(i,j) \quad (9)$$

Equation (10)
$$m_{11} = \sum_{i \in N_n} \sum_{j \in N_m} ij f(i,j) \quad (10)$$

Equation (11)
$$m_{02} = \sum_{j \in N_m} j^2 \sum_{i \in N_n} f(i,j) \quad (11)$$

In addition, the slope of the principal axis of inertia can be acquired by using the following Equation (12).

Equation (12)
$$\theta = \frac{1}{2}\tan^{-1} \frac{2m_{11}}{m_{02}-m_{20}} \quad (12)$$

In Equations (9) to (11) represented above, it is assumed that the size of the odd-field image is N×M, $N_n=\{1,2,\ldots,N\}$, and $N_m=\{1, 2, \ldots, M\}$. In the same manner described above, the slope of the principal axis of inertia of the even-field image can also be acquired. By calculating a difference between the slopes of the principal axes of inertia of the even-field image and the odd-field image, the amount of rotation can be acquired.

The enlargement factor can be acquired from a ratio of the moment of inertia of the even-field image to that of the odd-field image. In the same manner as described above, when the luminance of the pixel(i,j) of the odd-field image is f(i,j), the 0-th order moment of the odd-field image can be acquired by using the following Equation (13), and the first-order moment of the odd-field image can be acquired by using the following Equations (14) and (15).

Equation (13)
$$m_{00} = \sum_{i \in N_n} \sum_{j \in N_m} f(i, j) \quad (13)$$

Equation (14)
$$m_{10} = \sum_{i \in N_n} i \sum_{j \in N_m} f(i, j) \quad (14)$$

Equation (15)
$$m_{01} = \sum_{j \in N_m} j \sum_{i \in N_n} f(i, j) \quad (15)$$

Here, the center($i_G, j_G$) is $i_G = m_{10}/m_{00}$, and $j_G = m_{01}/m_{00}$. Accordingly, the moment of inertia of the odd-field image can be acquired by using the following Equation (16).

Equation (16)
$$\mu_f = \sum_{i \in N_n} \sum_{j \in N_m} ((i - i_G)^2 + (j - j_G)^2) f(i, j) \quad (16)$$

In the same manner as described above, the moment of inertia of the even-field image can also be acquired. In addition, the enlargement factor can be acquired by calculating the ratio of the moment of inertia of the even-field image to that of the odd-field image.

In this embodiment, the amount of shake of the image is calculated when an operation for the freeze is performed. However, it may be configured that the endoscope apparatus 1 generates a frame image in the live mode all the time, the even-field image and the odd-field image are generated from the frame image, and the amount of shake is calculated. In addition, it may be configured that a warning message is displayed on the monitor 4 or transition to the freeze state is suppressed in the case where the amount of shake exceeds a predetermined amount when the endoscope apparatus 1 is in the live mode. In addition, it may be configured that the amount of shake is determined when the endoscope apparatus 1 transits to the freeze state from the live mode, and a warning message and the like are displayed on the monitor 4 together with the frame image (still image) for a case where the amount of shake exceeds a predetermined amount.

In addition, in this embodiment, the amount of shake is calculated from the even-field image and the odd-field image. However, it may be configured that the amount of shake is calculated from video signals of two consecutive frames.

In the above description, the endoscope apparatus 1 according to this embodiment generates the frame image from the odd-field image or the even-field image. Alternatively, the endoscope apparatus 1 generates a corrected frame image acquired by correcting a video signal of at least one field of two fields constituting the frame image by the amount of shake. Accordingly, even when the shake of an image occurs in accordance with movement of the distal end of the endoscope 2 or an observation target, a frame image or a corrected frame image of which the amount of shake is less than that of the frame image generated by the frame image generation processing section 42 can be generated. As the measurement processing section 47 performs a measurement process based on the above-described frame image or the corrected frame image, a decrease in the measurement accuracy can be prevented.

In addition, in this embodiment, when the amount of shake is equal to or less than the first threshold value, the measurement processing section 47 performs a measurement process based on the frame image generated by the frame image generation processing section 42. On the other hand, when the amount of shake exceeds the first threshold value and is less than the second threshold value, the measurement processing section 47 performs a measurement process based on the frame image generated from the odd-field image or the even-field image or the corrected frame image. Accordingly, even when a large amount of shake occurs, a marked decrease in the accuracy of measurement can be prevented.

In addition, in this embodiment, an image on the basis of the frame image that is generated from the odd-field image or the even-field image or the corrected frame image is displayed on the monitor 4 at the time of measurement.

Accordingly, while viewing the image of which the amount of shake is reduced, the user designates a measurement point. Accordingly, it becomes easier for the user to designate the measurement point in a desired place, and a decrease in the measurement accuracy can be prevented.

In addition, in this embodiment, when the amount of shake is equal to or less than the second threshold value, the measurement process is permitted to be performed. On the other hand, when the amount of shake exceeds the second threshold value, the measurement process is prohibited to be performed. Accordingly, a decrease in the measurement accuracy can be prevented.

In addition, in this embodiment, when the amount of shake exceeds the second threshold value, a warning message and the like are displayed on the monitor 4. Accordingly, the user can notice that a frame image is not appropriate for measurement before the measurement is performed.

In other words, according to the present invention, by generating the second image from the first image based on the amount of shake, the second image of which the amount of shake is less than that of the first image can be generated. By measuring the subject based on the second image, a decrease in the measurement accuracy can be prevented.

While the exemplary embodiments of the invention have been described with reference to the accompanying drawings, the detailed constitutions of the invention are not limited to the foregoing embodiments but embrace changes in design to the extent that they do not depart from the concept of the invention.

What is claimed is:
1. An endoscope apparatus comprising:
   an imaging unit which comprises an imaging device and generates a first image having two fields by imaging a subject by performing interlaced driving for the imaging device;

a detection unit which detects an amount of shake of the first image;

a process unit which generates a second image from the first image based on the amount of shake;

a measurement unit which measures the subject based on the second image;

a display unit which displays the second image generated by the process unit after displaying the first image; and an operation direction unit which is operable by a user to input an operation direction, wherein when the first image is displayed by the display unit and a first operation direction is input to the operation direction unit, the display unit continues to display the first image and displays an index which represents the amount of shake of the first image which is detected by the detection unit.

2. The endoscope apparatus according to claim 1, wherein when the display unit continues to display the first image in accordance with the first operation direction and a second operation direction is input to the operation direction unit, the process unit generates the second image based on the amount of shake, and the display unit displays the second image instead of the first image.

3. An endoscope apparatus comprising:

an imaging unit which comprises an imaging device and generates a first image having two fields by imaging a subject by performing interlaced driving for the imaging device;

a detection unit which detects an amount of shake of the first image;

a process unit which generates a second image from the first image based on the amount of shake;

a measurement unit which measures the subject based on the second image; and a control unit which prohibits measurement to be performed by the measurement unit in a case where the amount of shake exceeds a predetermined amount.

4. The endoscope apparatus according to claim 3, further comprising:

a display unit;

wherein the control unit controls the display unit to display a warning message when the amount of shake exceeds the predetermined amount.

5. The endoscope apparatus according to claim 4, wherein the control unit controls the display unit to display the warning message with the first image.

6. The endoscope apparatus according to claim 3, further comprising:

a display unit;

wherein the control unit controls the display unit to display a value of the amount of shake when the amount of shake exceeds the predetermined amount.

7. The endoscope apparatus according to claim 6, wherein the control unit controls the display unit to display a warning message with the value of the amount of shake.

* * * * *